United States Patent
Lu et al.

(10) Patent No.: US 10,059,935 B2
(45) Date of Patent: Aug. 28, 2018

(54) **COMPOSITE OF *PARACOCCUS DENITRIFICANS* IMMOBILIZED ON MODIFIED GRAPHENE OXIDE AND ITS PREPARATION METHOD AND APPLICATION**

(71) Applicant: Soochow University, Suzhou, Jiangsu (CN)

(72) Inventors: Jianmei Lu, Jiangsu (CN); Dongyun Chen, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 159 days.

(21) Appl. No.: 15/382,625

(22) Filed: Dec. 17, 2016

(65) Prior Publication Data
US 2017/0175100 A1    Jun. 22, 2017

(30) Foreign Application Priority Data
Dec. 17, 2015  (CN) .......................... 2015 1 0957637

(51) Int. Cl.
| | | |
|---|---|---|
| *C12N 11/14* | (2006.01) | |
| *C12N 1/20* | (2006.01) | |
| *C02F 3/28* | (2006.01) | |
| *C02F 3/30* | (2006.01) | |
| *C02F 3/34* | (2006.01) | |
| *C02F 101/30* | (2006.01) | |
| *C02F 101/38* | (2006.01) | |

(Continued)

(52) U.S. Cl.
CPC ............ *C12N 11/14* (2013.01); *C02F 3/2806* (2013.01); *C02F 3/305* (2013.01); *C12N 1/20* (2013.01); *C02F 3/341* (2013.01); *C02F 2101/306* (2013.01); *C02F 2101/38* (2013.01); *C02F 2103/24* (2013.01); *C02F 2103/343* (2013.01); *C02F 2103/36* (2013.01)

(58) Field of Classification Search
None
See application file for complete search history.

(56) References Cited

U.S. PATENT DOCUMENTS

| 3,573,122 | A | * | 3/1971 | Olstowski | ............... | H01B 1/24 264/105 |
|---|---|---|---|---|---|---|
| 5,360,522 | A | * | 11/1994 | Kuroda | .................. | C02F 3/005 205/759 |

(Continued)

FOREIGN PATENT DOCUMENTS

WO    WO-9220789 A1 * 11/1992 ............... A23B 4/22

*Primary Examiner* — Renee Claytor
*Assistant Examiner* — Trent R Clarke
(74) *Attorney, Agent, or Firm* — SZDC Law P.C.

(57) ABSTRACT

This invention provided a preparation method of the composite which was immobilized *Paracoccus denitrificans* on modified graphene oxide and its application. The composite was obtained by following the steps below: 1) Synthesis of graphene oxide; 2) Synthesis of modified graphene oxide; 3) Acclimatization and immobilization of *Paracoccus denitrificans*. In this invention, the raw materials were low-cost and easily obtained used in the preparation process; easy operation, convenient, and no expensive instruments during the whole process; this invention of the composite could remove DMF from wastewater completely, and with the advantages of high efficiency, good recycle performance, economical, environmentally friendly, better feasibility.

Figure 1:
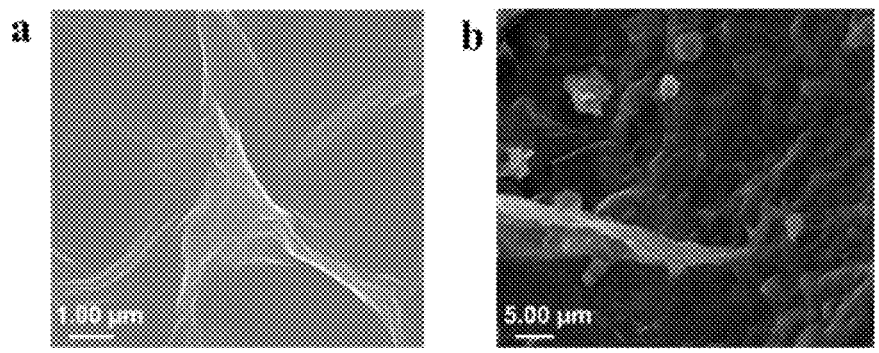

10 Claims, 2 Drawing Sheets a b

(51) Int. Cl.
  *C02F 103/24* (2006.01)
  *C02F 103/34* (2006.01)
  *C02F 103/36* (2006.01)

(56) References Cited

U.S. PATENT DOCUMENTS

| | | | |
|---|---|---|---|
| 2005/0020759 A1* | 1/2005 | Gotou | C08K 3/04 524/495 |
| 2011/0133132 A1* | 6/2011 | Zhamu | B82Y 30/00 252/503 |
| 2013/0330833 A1* | 12/2013 | Ruiz | B01D 39/00 436/174 |

* cited by examiner

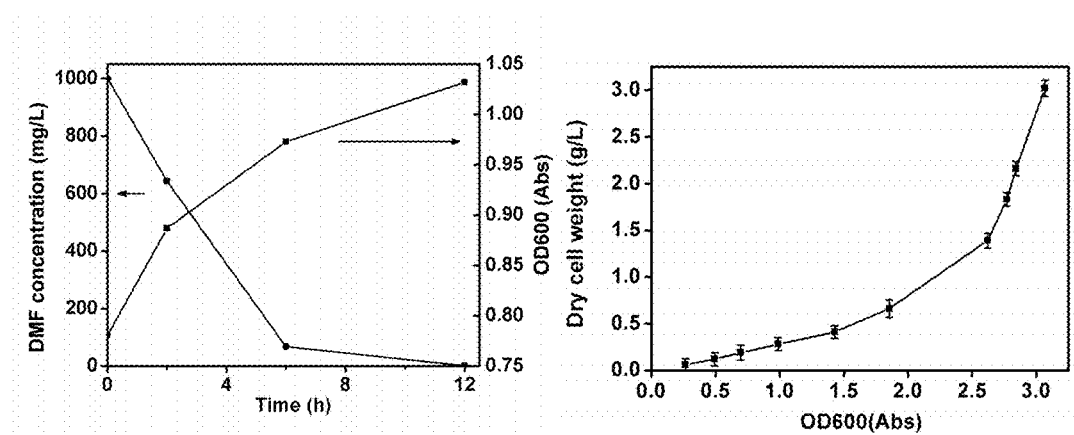
Figure 6
Figure 7
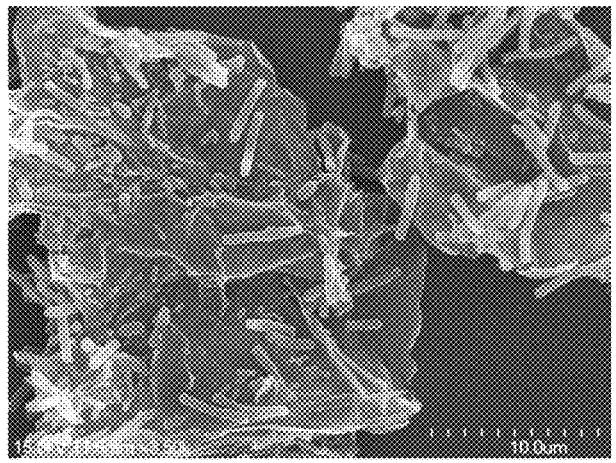
Figure 8
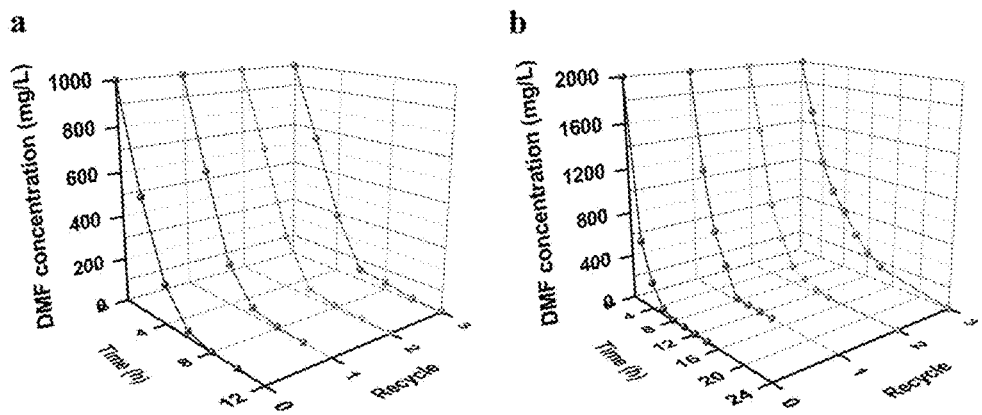
Figure 9

COMPOSITE OF *PARACOCCUS DENITRIFICANS* IMMOBILIZED ON MODIFIED GRAPHENE OXIDE AND ITS PREPARATION METHOD AND APPLICATION

This application claims priority to Chinese Patent Application No. 201510957637.4, filed on Dec. 17, 2015, which is incorporated by reference for all purposes as if fully set forth herein.

TECHNICAL FIELD

The invention belongs to the field of functional materials, specifically including a composite which immobilized bacteria (especially *Paracoccus denitrificans*) on modified graphene oxide, preparation method of the composite, and its application in the treatment of high-concentrated DMF.

BACKGROUND TECHNOLOGY

The problems of environmental pollution become serious with the rapid development of global economy. The wastewater in industrial fields containing considerable amounts of N, N-dimethylformamide (DMF), such as pharmaceutical, pesticide, petrifaction, leather industries, etc. Among these, the amount of discharged water containing DMF from leather industries reached one hundred million tons per year. DMF can enter into body through the respiratory tract, digestive tract and skin system, which is toxic. DMF is regarded as level II (moderate hazard level) according to classification for hazards of occupational exposure to toxicant, which becomes a carcinogen to experimental animals. In the process of daily production, DMF which is chemically nonreactive is usually used as an organic solvent, so there is no loss in dosage. Moreover, all of the DMF will pour into industry wastewater after production and exist stably for a long time. Therefore, if the problem is not solved, it will cause great pollution to environment.

Adsorption is a common method for the treatment of wastewater containing DMF, which has many advantages, such as short process, easy operation, good treatment efficiency, etc. But, it need to desorption of adsorbent after adsorption, and the cost is high and even cause secondary pollution. Furthermore, the adsorbent can reach a maximal equilibrium adsorption amount but cannot remove pollutant completely. Therefore, biodegradation method comes in to being to resolve the problems mentioned above, which has advantages in high efficiency, economical, environmentally friendly, strong stability and so on. However, high-concentrated DMF (2000 mg/L) have toxic to bacterial cells, which causes the negative effect in treatment efficiency during the treatment and limits the practical application.

Therefore, it is imperative to find a new strategy to deal with high-concentrated DMF in wastewater with the advantages of economical, high efficiency and stability.

INVENTION CONTENT

In response to these circumstances, this invention designed a new system by combing the advantage of adsorption and biodegradation. The synthetic material (modified graphene oxide prepared via free radical solution polymerization) was not only act as a high-capable adsorbent for DMF but also a carrier for the immobilization of bacterial cells (*Paracoccus denitrificans*) in the treatment of DMF. This new composite method not only solved the problems of regeneration of adsorbent and cannot remove pollutant completely, but also struck down the limitation in DMF concentration of biodegradation method. Furthermore, this new composite method lowered the cost of treatment and avoided secondary pollution.

First, this invention provided a preparation method of the composite which was immobilized *Paracoccus denitrificans* on modified graphene oxide. The steps were described below:

(1) Synthesis of Graphene Oxide (GO):

Graphite (1 g) was mixed in concentrated $H_2SO_4$ (20-25 mL) and the mixture was cooled using an ice bath to 0° C. and stirred continually. Then, $KMnO_4$ (graphite:$KMnO_4$=1: 5-8 in mass ratio) was added to the suspension in batch, and the reaction system was kept at 35-40° C. and stirred for 15-20 h. After that, the reaction mixture was poured into ice water containing $H_2O_2$, and then was centrifuged, washed and dried to obtain GO;

(2) Synthesis of Modified Graphene Oxide (PGO):

GO obtained from step (1) and triethylamine (triethylamine:methacryloyl chloride=1:1 in stoichiometric molar ratio) were were dispersed in dimethylacetamide under inert gas conditions at 0° C. and stirred continually. Then the mixture of methacryloyl chloride (GO:methacryloyl chloride=1:0.5-1.5 in mass ratio) and dimethylacetamide were added to the reaction system and kept at room temperature and stirred for 20-24 h. Subsequently, the product was centrifuged, washed and dried to obtain acylated GO;

Next, the acylated GO (acylated GO:methacrylic acid=1: 0.5-2.5 in mass ratio) was dispersed in DMF under inert gas conditions. Then, the monomers mixture (methacrylic acid and butyl methacrylate) and the initiator (methacrylic acid: butyl methacrylate:azobisisobutyronitrile=50:50-100:1-2 in stoichiometric molar ratio) were added into the reaction system, the free radical solution polymerization was proceeded at 60-70° C. for 8-10 h. The mixture was precipitated in ether, and then was filtered, dried to obtain PGO;

(3) Acclimatization and Immobilization of *Paracoccus denitrificans*:

The cells of *Paracoccus denitrificans* were harvested and then transferred in 1000 mg/L of glucose solution, and the acclimatization process was achieved by following method: increased the DMF concentration (100 mg/L) and in the meanwhile decreased the glucose concentration (100 mg/L) gradually per 3-6 days until 0 mg/L of glucose concentration. And constantly increased the DMF concentration up to 2000 mg/L and completed the acclimatization process;

PGO obtained from step (2) and N-hydroxy succinimide were dispersed in DMF. Then N,N'-Dicyclohexylcarbodiimide (PGO:N-hydroxy succinimide:N,N'-Dicyclohexylcarbodiimide=1:1-2:1-3 in mass ratio) and 4-dimethylaminopyridine (N,N'-Dicyclohexylcarbodiimide:4-dimethylaminopyridine=1:1 in stoichiometric molar ratio) and stirred for 24 h at room temperature to obtain amidated PGO;

The amidated PGO and acclimatized bacteria (amidated PGO:acclimatized bacteria=1:1-3 in mass ratio) were added into the Phosphate Buffered Saline (PBS) solution and incubated at 30° C. for 20-24 h to get composite which immobilized *Paracoccus denitrificans* on modified graphene oxide.

Preferable, in the preparation method above, the ratio of graphite:concentrated $H_2SO_4$=1 g:23 mL mentioned in step (1).

Preferable, in the preparation method above, the mass ratio of graphite:$KMnO_4$=1:6 mentioned in step (1).

Preferable, in the preparation method above, $KMnO_4$ was added in 2 batches with the same weight mentioned in step (1).

Preferable, in the preparation method above, chose any one of different inert gas mentioned in step (2), including nitrogen, helium and argon. However, nitrogen was preferred.

Preferable, in the preparation method above, the mass ratio of GO:methacryloyl chloride=1:1 mentioned in step (2).

Preferable, in the preparation method above, the mass ratio of acylated GO:methacrylic acid=1:0.5 mentioned in step (2).

Preferable, in the preparation method above, the stoichiometric molar ratio of methacrylic acid:butyl methacrylate: azobisisobutyronitrile=50:50:1 mentioned in step (2).

Preferable, in the preparation method above, the mass ratio of PGO:N-hydroxy succinimide:N,N'-Dicyclohexylcarbodiimide=1:1:3 mentioned in step (3).

Preferable, in the preparation method above, the mass ratio of amidated PGO:*Paracoccus denitrificans*=1:2 mentioned in step (3).

Preferable, in the preparation method above, adjusted the pH of PBS solution to 7 mentioned in step (3).

Next, this invention provided a preparation method of the composite which immobilized *Paracoccus denitrificans* on modified graphene oxide mentioned above.

Finally, this invention provided the application of the composite which immobilized *Paracoccus denitrificans* on modified graphene oxide in the treatment of wastewater containing DMF, especially the high-concentrated DMF. Moreover, the maximum concentration of DMF reached 2000 mg/L as mentioned above.

Compared with existing technologies, this invention based on the technical option above had the advantages as followed:

(1) The raw materials were low-cost and easily obtained used in the preparation process;

(2) Easy operation, conveniency, and no expensive instruments during the whole process;

(3) This invention of the composite could remove DMF from wastewater completely, and with the advantages of high efficiency, good recycle performance, economical, environmentally friendly, better feasibility.

FIGURE ILLUSTRATION

FIG. 1. SEM images of GO and PGO.

Figure 2:
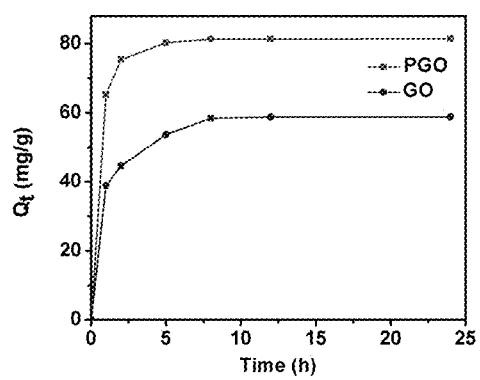

FIG. 2. Adsorption capacity for DMF varied with time of GO and PGO.

Figure 3:
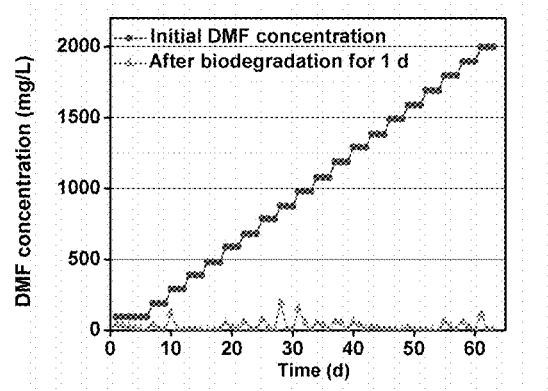

FIG. 3. Acclimatization of *Paracoccus denitrificans*.

Figure 4:
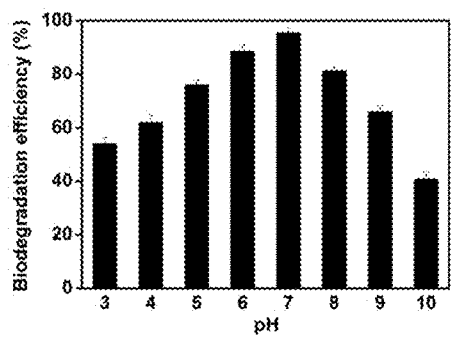

FIG. 4. Effect of pH on the biodegradation efficiency of DMF by *Paracoccus denitrificans*.

Figure 5:
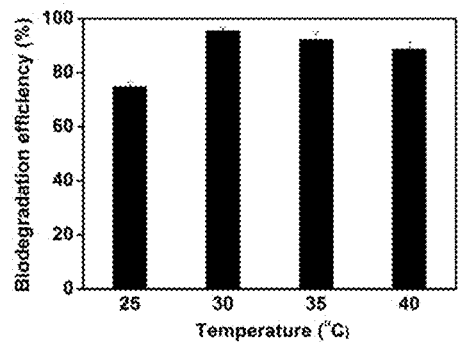

FIG. 5. Effect of temperature on the biodegradation efficiency of DMF by *Paracoccus denitrificans*.

FIG. 6. Biodegradation of DMF by *Paracoccus denitrificans* under optimal conditions.

FIG. 7. The relation of OD600 and dry cell weight of *Paracoccus denitrificans*.

FIG. 8. SEM image of *Paracoccus denitrificans* immobilized on PGO.

FIG. 9. The degradation and recycle performance of *Paracoccus denitrificans* immobilized on PGO in the treatment of DMF (1000 mg/L, 2000 mg/L).

SPECIFIC IMPLEMENTATION METHOD

The invention will be made a further explanation according to the following figures and the specific implementations. The chemicals, materials and instruments used in the following implementations were obtained commercially unless were specifically explained.

Implementation 1: Synthesis of GO.

Graphite (3 g) was mixed in concentrated $H_2SO_4$ 69 mL) and the mixture was cooled using an ice bath to 0° C. and stirred continually for 2 h. Then, $KMnO_4$ (9.0 g) was added to the suspension in batch slowly to keep the reaction temperature lower than 20° C. and the reaction system was warmed to 35° C. and vigorously stirred for 7 h. Next, additional $KMnO_4$ (9.0 g) was added in one portion and the reaction was still stirred for 12 h. After that, the reaction mixture was poured into ice water (400 mL), then $H_2O_2$ was added dropwise to obtain yellow mixture. Then the mixture was centrifuged and washed with HCl (5%) and deionized water for 3 times respectively. The product was dried in vacuum desiccator to obtain GO (4 g).

Implementation 2: Synthesis of PGO.

The dried GO (1 g) obtained in implementation 1 and triethylamine (0.01 mol) were dispersed in dimethylacetamide under $N_2$ atmospheric conditions. Then the mixture of methacryloyl chloride (1 g, 0.01 mol) and dimethylacetamide were added dropwise to the reaction system through a constant pressure funnel and stirred for 0.5 h at 0° C. Then the reaction system was warm to room temperature and stirred for 24 h. Subsequently, the product was centrifuged, washed with acetone for 2 times and dried in vacuum desiccator for 12 h to obtain acylated GO.

Next, the acylated GO was dispersed in DMF. Then, the monomers mixture (methacrylic acid, 0.5 g, 0.006 mol; butyl methacrylate, 0.006 mol) and the initiator (azobisisobutyronitrile, 0.12 mol) were added into the reaction system under $N_2$ atmospheric conditions, the free radical solution polymerization was proceeded at 70° C. for 8 h. The mixture was precipitated in ether, and then was filtered, dried in vacuum desiccator at 45° C. for 12 h to obtain PGO (1.8 g). The polymers on the surface of PGO could form the Van der Waals force with DMF molecules and improved the adsorption capacity.

FIG. 1*a* showed the SEM image of GO, which presented a laminated structure with smooth surface and wrinkled edge. FIG. 1*b* showed the SEM image of PGO, showed a significantly rougher surface than GO, which suggested that the polymers were successfully grafted to the surface of GO.

Implementation 3: Adsorption Capacity of Adsorbents.

The equilibrium adsorption experiments were carried out in the 250 mL flasks containing 100 mg of diverse adsorbents (GO and PGO) and 50 mL aqueous solution with an initial DMF concentration of 1000 mg/L at 30° C. As shown in FIG. 2, the maximal equilibrium adsorption amount of PGO was significantly increased by 40% compared with GO.

Implementation 4: Acclimatization of *Paracoccus denitrificans*.

The strain of *Paracoccus denitrificans* (ATCC 19367, Shanghai Fuxiang Biotechnology Co., Ltd.) was inoculated in the LB liquid medium (Tryptone, 10 g/L; Yeast extract, 5 g/L; NaCl, 10 g/L). The bacteria were harvested by centrifuging and then transferred in a 50 mL MM1 solution ($K_2HPO_4$, 6.3 g/L; $KH_2PO_4$, 1.8 g/L; $MgSO_4 \cdot 7H_2O$, 0.1 g/L; $MnSO_4 \cdot 4H_2O$, 0.1 g/L; $CaCl_2 \cdot 2H_2O$, 0.1 g/L; $FeSO_4 \cdot 7H_2O$, 0.1 g/L; $Na_2MoO_4 \cdot 2H_2O$, 0.006 g/L) with 1000 mg/L of glucose and incubated at 30° C., 150 r/min for 24 h. The acclimatization process was accomplished by increasing the DMF concentration (100 mg/L every time) gradually and in the meanwhile decreasing the glucose concentration (100 mg/L every time) gradually and inoculated for 6 days. Then adjusted the concentration every 3 days from the 7th day until 0 mg/L of glucose concentration. And constantly increased the DMF concentration up to 2000 mg/L and completed the acclimatization process. As showed in FIG. 3, the strain was capable of utilizing DMF as a sole source of carbon and nitrogen, and the maximum concentration of DMF reached 2000 mg/L.

Implementation 5: Biodegradation of DMF by *Paracoccus denitrificans*.

Before the biodegradation experiments, the optimal conditions of the biodegradation of DMF by *Paracoccus denitrificans* cells need to be determined first. Batch experiments were carried out at different pH (3-10) and temperatures (25-40° C.) respectively in the other same conditions. Bacterial cells (wet weight=2 g) were added to the 250 mL Erlenmeyer flasks containing the same initial DMF concentration of 1000 mg/L (50 mL) and incubated at 30° C. on the constant temperature oscillator to investigate the effects of pH and temperature. The biodegradation efficiency of free cells was detected under the optimal conditions of pH and temperature and the value of OD600 was detected by UV-Vis spectrophotometer at the wavelength of 600 nm.

FIG. 4 and FIG. 5 showed the effects of pH and temperature on biodegradation efficiency of DMF by *Paracoccus denitrificans* respectively, indicated that it had a best biodegradation rate at the optimized temperature of 30° C. and the optimum pH value near neutrality. FIG. 6 showed the biodegradation curve and OD600 of free *Paracoccus denitrificans* with the same initial DMF concentration of 1000 mg/L under the optimal conditions. It could be seen that free cells of *Paracoccus denitrificans* were able to degrade DMF completely within 12 h when the initial concentration was 1000 mg/L. And the increase amount of bacterial cells in FIG. 4 was calculated according to the relative conversion curve of OD600 and dry cell weight (FIG. 7) as 7 mg.

Implementation 6: Immobilization of *Paracoccus denitrificans*

PGO (1 g) obtained in implementation 2 and N-hydroxy succinimide (1 g) were dispersed in DMF. Then N,N'-Dicyclohexylcarbodiimide (3 g, 0.015 mol) and 4-dimethylaminopyridine (1.8 g, 0.015 mol) and stirred for 24 h at room temperature and washed with PBS solution for 3 times. The product and acclimatized bacteria (the mass ratio of PGO:acclimatized bacteria=1:2) obtained in implementation 5 were added into the PBS solution (pH=7) together and incubated at 30° C. for 24 h. The bacterial cells which had many innate amine groups on the surface could be immobilized onto PGO stably which contained many carboxyl groups (—COOH) on the surface by direct covalent chemical conjugation. And the composite of *Paracoccus denitrificans* immobilized on PGO was achieved.

FIG. 8 showed the SEM image of *Paracoccus denitrificans* immobilized on PGO. It cold be seen the bacteria were immobilized on the PGO successfully.

Implementation 7: Adsorption-Biodegradation Capability and Recycle Performance of *Paracoccus denitrificans* Immobilized on PGO to DMF.

Bacterial cells immobilized on PGO (wet weight=2 g) were added to the 250 mL Erlenmeyer flasks containing DMF (1000 mg/L, 2000 mg/L) (50 mL MM1 solution) and tested the adsorption-biodegradation capability and recycle performance.

FIG. 9a and FIG. 9b showed the adsorption-biodegradation and recycle process of cells immobilized on PGO for the initial DMF concentrations of 1000 mg/L and 2000 mg/L, respectively. After recycling for 3 times, DMF still could be removed completely from aqueous solutions by cells immobilized on PGO, which presented a good practicability.

In conclusion, this invention provided a preparation method of *Paracoccus denitrificans* immobilized on modified graphene oxide, which could remove DMF (2000 mg/L) from aqueous solutions completely by simultaneous adsorption-biodegradation process. Moreover, the treatment method in this invention had the advantages of easy operation, economical, environmentally friendly, good recycle performance, which will have a great prospect in the treatment process of wastewater in the future.

The invention claimed is:
1. A method of preparing a composite which has *Paracoccus denitrificans* immobilized on modified graphene oxide, comprising:
  1) synthesis of graphene oxide:
    add graphite into concentrated $H_2SO_4$ in accordance with the ratio of every 1 g graphite:20-25 mL concentrated $H_2SO_4$, while cooling with an ice bath to 0° C. and stirring continually, then, in accordance with a mass ratio of graphite:$KMnO_4$=1:5-8, add $KMnO_4$ to the suspension of graphite and $H_2SO_4$ in a batch, and keep the suspension at 35-40° C. and stir for 15-20 h, after that, pour the suspension into ice water containing $H_2O_2$, and centrifuge, wash and dry to obtain the graphene oxide;
  2) synthesis of modified graphene oxide:
    in accordance with graphene oxide:methacryloyl chloride=1:0.5-1.5 in mass ratio and triethylamine:methacryloyl chloride=1:1 in stoichiometric molar ratio, disperse said graphene oxide obtained in step 1) in dimethylacetamide with triethylamine under inert gas conditions at 0° C. and stir continually, then add a mixture of methacryloyl chloride and dimethylacetamide and keep at room temperature and stir for 20-24 h, subsequently, centrifuge, wash and dry the product to obtain an acylated graphene oxide;
    in accordance with acylated graphene oxide:methacrylic acid=1:0.5-2.5 in mass ratio and methacrylic acid:butyl methacrylate:azobisisobutyronitrile=50:50-100:1-2 in stoichiometric molar ratio, disperse the acylated graphene oxide in dimethylformamide (DMF) under inert gas conditions, then, add methacrylic acid, butyl methacrylate and an initiator, allow free radical solution to polymerize at 60-70° C. for 8-10 h, precipitate the resulting reaction mixture in ether, and then filter and dry to obtain the modified graphene oxide;
  3) acclimatization and immobilization of *Paracoccus denitrificans*:
    harvest cells of *Paracoccus denitrificans* which were grown in liquid medium with 1000 mg/L of glucose solution, and acclimatize by the following method: increase the DMF concentration by 100 mg/L while decreasing the glucose concentration by 100 mg/L every 3-6 days, until the glucose concentration reaches 0 mg/L, and the DMF concentration reaches 2000 mg/L, completing the acclimatization process;
    in accordance with the modified graphene oxide:N-hydroxy succinimide:N,N'-Dicyclohexylcarbodiimide=1:1-2:1-3 in mass ratio, and N,N'-Dicyclohexylcarbodiimide:4-dimethylaminopyridine=1:1 in stoichiometric molar ratio, disperse the modified graphene oxide obtained in step 2) and N-hydroxy succinimide in DMF, then add N,N'-Dicyclohexylcarbodiimide and 4-dimethylaminopyridine, stir for 24 h at room temperature to obtain amidated modified graphene oxide;

in accordance with amidated modified graphene oxide: acclimatized bacteria=1:1-3 in mass ratio, add the amidated modified graphene oxide and acclimatized bacteria into a phosphate buffered saline (PBS) solution and incubate at 30° C. for 20-24 h to get the composite which has *Paracoccus denitrificans* immobilized on modified graphene oxide.

2. The method according to claim 1, wherein:
in step 1), the ratio of graphite:concentrated $H_2SO_4$=1 g:23 mL,
in step 1), the mass ratio of graphite:$KMnO_4$=1:6,
in step 1), $KMnO_4$ was added in 2 batches with the same weight.

3. The method according to claim 1, wherein: in step 2), said inert gas is any one of nitrogen, helium and argon.

4. The method according to claim 3, wherein: in step 2), said inert gas is nitrogen.

5. The method according to claim 1, wherein:
in step 2), the mass ratio of graphene oxide:methacryloyl chloride=1:1,
in step 2), the mass ratio of acylated graphene oxide: methacrylic acid=1:0.5,
in step 2), the stoichiometric molar ratio of methacrylic acid:butyl methacrylate:azobisisobutyronitrile=50:50:1.

6. The method according to claim 1, wherein:
in step 3), the mass ratio of modified graphene oxide:N-hydroxy succinimide:N,N'-Dicyclohexylcarbodiimide=1:1:3,
in step 3), the mass ratio of amidated modified graphene oxide:*Paracoccus denitrificans*=1:2.

7. The method according to claim 1, wherein:
in step 3), the pH of PBS solution equals 7.

8. A composite which has *Paracoccus denitrificans* immobilized on modified graphene oxide prepared according to the preparation method of claim 1.

9. A method of treating DMF waste water comprising applying the composite of claim 8 to the DMF waste water.

10. The method according to claim 9, wherein:
the maximum concentration of DMF in the DMF waste water is 2000 mg/L.

* * * * *